United States Patent

Murray

[11] Patent Number: 5,616,146
[45] Date of Patent: Apr. 1, 1997

[54] METHOD AND APPARATUS FOR MACHINING BONE TO FIT AN ORTHOPEDIC SURGICAL IMPLANT

[76] Inventor: William M. Murray, 5020 Ritter Rd., Suite 211, Mechanicsburg, Pa. 17055-4837

[21] Appl. No.: 243,508

[22] Filed: May 16, 1994

[51] Int. Cl.$^6$ .................................. A61B 17/56
[52] U.S. Cl. .................. 606/80; 606/88; 606/87; 606/102
[58] Field of Search .................. 606/88, 87, 89, 606/96, 102, 105, 80, 82, 84, 79, 57, 58, 59

[56] References Cited

U.S. PATENT DOCUMENTS

| | | | |
|---|---|---|---|
| D. 346,979 | 5/1994 | Stalcup et al. | D10/64 |
| 2,267,157 | 12/1941 | Lippincott . | |
| 4,467,801 | 8/1984 | Whiteside . | |
| 4,474,177 | 10/1984 | Whiteside . | |
| 4,487,203 | 12/1984 | Androphy . | |
| 4,550,448 | 11/1985 | Kenna | 623/16 |
| 4,565,192 | 1/1986 | Shapiro | 606/88 X |
| 4,574,794 | 3/1986 | Cooke et al. . | |
| 4,633,862 | 1/1987 | Petersen . | |
| 4,667,664 | 5/1987 | Taylor et al. . | |
| 4,703,751 | 11/1987 | Pohl . | |
| 4,706,660 | 11/1987 | Petersen . | |
| 4,708,139 | 11/1987 | Dunbar, IV . | |
| 4,718,414 | 1/1988 | Saunders et al. . | |
| 4,721,104 | 1/1988 | Kaufman et al. . | |
| 4,738,254 | 4/1988 | Buechel et al. . | |
| 4,788,970 | 12/1988 | Kara et al. . | |
| 4,791,919 | 12/1988 | Elloy et al. . | |
| 4,834,080 | 5/1989 | Brown . | |
| 4,873,974 | 10/1989 | Hagen et al. . | |
| 4,911,153 | 3/1990 | Border | 606/98 |
| 4,952,213 | 8/1990 | Bowman et al. | 606/79 |
| 4,976,713 | 12/1990 | Landanger et al. | 606/62 |
| 5,002,547 | 3/1991 | Poggie et al. | 606/88 |
| 5,007,912 | 4/1991 | Albrektsson et al. | 606/87 |
| 5,021,055 | 6/1991 | Burkinshaw et al. | 606/82 |
| 5,035,699 | 7/1991 | Coates | 606/86 |
| 5,042,983 | 8/1991 | Rayhack | 606/87 |
| 5,047,032 | 9/1991 | Jellicoe | 606/83 |
| 5,047,033 | 9/1991 | Fallin | 606/87 |
| 5,049,151 | 9/1991 | Durham et al. | 606/98 |
| 5,053,037 | 10/1991 | Lackey | 606/79 |
| 5,067,898 | 11/1991 | Dury . | |
| 5,098,436 | 3/1992 | Ferrante et al. | 606/88 |
| 5,100,404 | 3/1992 | Hayes | 606/62 |

(List continued on next page.)

FOREIGN PATENT DOCUMENTS 8804912  7/1988  WIPO .

OTHER PUBLICATIONS

The Anspach Effort, Inc. instructional pamphlet entitled "The 65K Univerisal Instrument System and Neuro System" (2 pp.) Date and Author unknown.

The Anspach Effort, Inc. Price List published Dec., 1992 (2 pp.) Author unknown.

*Primary Examiner*—Guy V. Tucker
*Attorney, Agent, or Firm*—Webb Ziesenheim Bruening Logsdon Orkin & Hanson, P.C.

[57] ABSTRACT

An apparatus for retaining a bone site in a fixed position and guiding a high speed power tool for machining the bone, such as a patella, including a positioner frame for rigid attachment about the bone site. The frame includes a bone clamping mechanism capable of adjustment and orientation of the bone site relative to the frame. A hinged power tool mount attaches to the frame and is adapted to receive a power tool for machining the bone in a predetermined manner. A power tool is received by the mount. A template corresponding to the predetermined manner attaches to the positioner frame for guiding the power tool. The bone clamping mechanism includes a plurality of gripping assemblies adapted to grip the bone about multiple locations. A depth adjustment guide is provided in the frame, which is adapted to cooperate with the power tool for controlling the depth the cut. A method for using the apparatus is also disclosed.

27 Claims, 7 Drawing Sheets

U.S. PATENT DOCUMENTS

| | | | |
|---|---|---|---|
| 5,100,409 | 3/1992 | Coates et al. | 606/88 |
| 5,108,396 | 4/1992 | Lackey et al. | 606/62 |
| 5,108,401 | 4/1992 | Insall et al. | 606/79 |
| 5,108,405 | 4/1992 | Mikhail et al. | 606/96 |
| 5,112,335 | 5/1992 | Laboureau et al. | 606/88 |
| 5,112,336 | 5/1992 | Krevolin et al. | 606/96 |
| 5,116,338 | 5/1992 | Poggie et al. | 606/90 |
| 5,122,144 | 6/1992 | Bert et al. | 606/88 |
| 5,129,907 | 7/1992 | Heldreth et al. | 606/80 |
| 5,129,908 | 7/1992 | Petersen | 606/88 |
| 5,141,513 | 8/1992 | Fortune et al. | 606/96 |
| 5,147,365 | 9/1992 | Whitlock et al. | 606/88 |
| 5,154,717 | 10/1992 | Matsen, III et al. | 606/53 |
| 5,160,335 | 11/1992 | Wagenknecht | 606/59 |
| 5,190,547 | 3/1993 | Barber, Jr. et al. | 606/79 |
| 5,207,680 | 5/1993 | Dietz et al. | 606/86 |
| 5,207,682 | 5/1993 | Cripe | 606/96 |
| 5,228,459 | 7/1993 | Caspari et al. | 128/898 |
| 5,342,364 | 8/1994 | Mikhail | 606/79 |
| 5,344,423 | 9/1994 | Dietz et al. | 606/87 |
| 5,380,332 | 1/1995 | Ferrante | 606/79 |

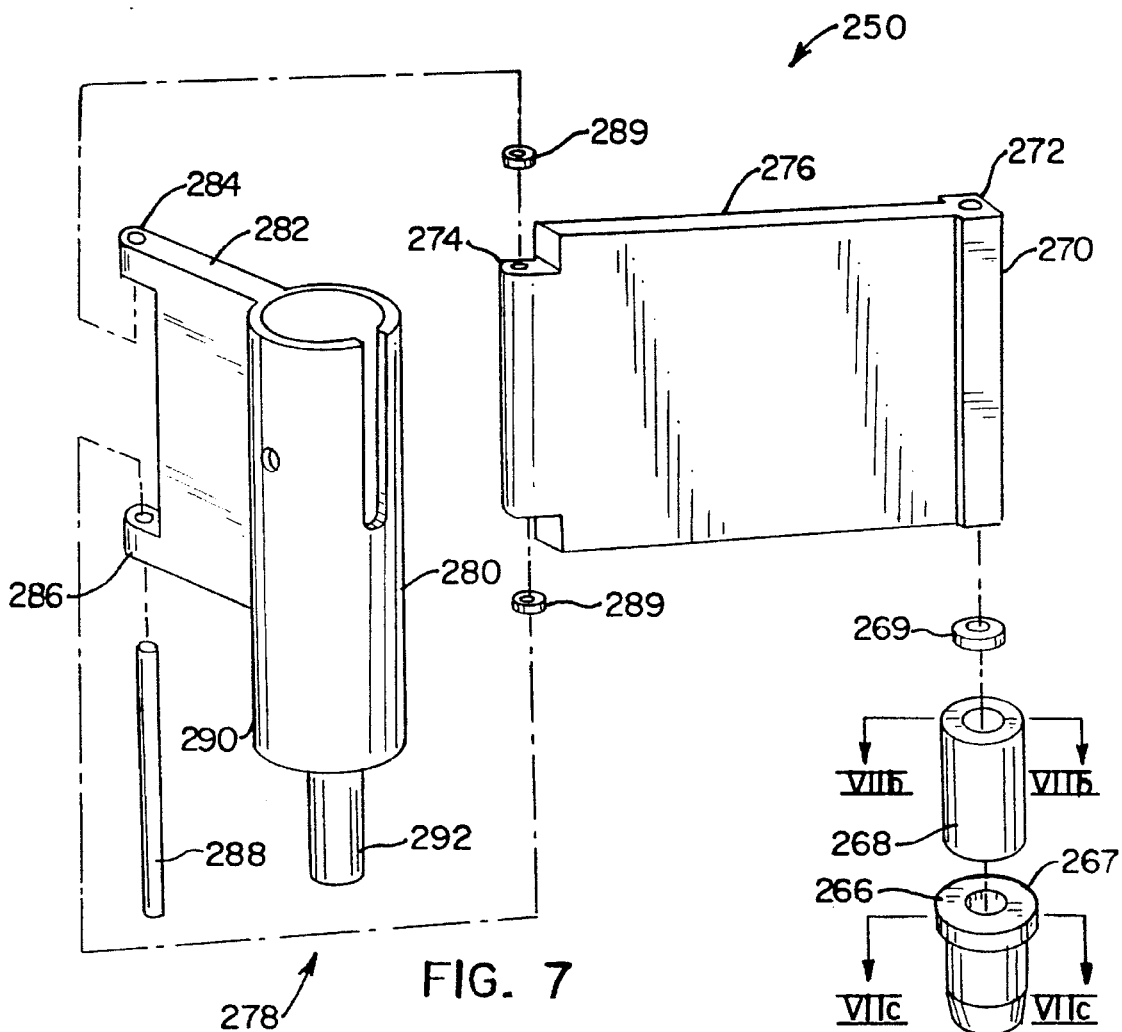

METHOD AND APPARATUS FOR MACHINING BONE TO FIT AN ORTHOPEDIC SURGICAL IMPLANT

BACKGROUND OF THE INVENTION

1. Field of the Invention

This invention relates generally to a method and apparatus for machining bone to fit an orthopedic surgical implant, and more particularly to a method and apparatus for machining a patella to fit a patellar implant.

2. Description of the Prior Art

The human knee joint sustains enormous stress even under ordinary circumstances, causing inevitable joint degeneration over time, and disease and aging only exacerbate this process. The surgical procedure termed "total knee arthroplasty" (colloquially known as knee replacement surgery) is therefore understandably common, and has been performed with increasing frequency in recent years.

The knee is formed where the femur meets the tibia. The head of the tibia includes two condyles that form two smooth concave surfaces which articulate with the condyles of the femur. The patella is a sesamoid (lens shaped) bone which slides in a groove located between the condyles of the femur and developed in the tendon of the quadriceps femoris muscle. The patella functions to increase the efficiency of the quadriceps muscle. As the knee articulates, the muscles and tendons force the patella toward the condyles of the femur.

Total knee arthroplasty replaces degenerate femoral condyles, and degenerate tibial plateau surfaces with prosthetic implants and, when necessary, the articular surface of the patella can also be replaced. When the latter is necessary, commonly an ultra-high molecular weight polyethylene articulating surface, with or without a metal baseplate, is implanted on the posterior side of the patella, adjacent the femoral condyles. This surgical procedure requires the knee to be approached through a longitudinal skin incision, followed by a medial parapatellar capsular incision. The quadriceps tendon is then incised longitudinally, allowing eversion and dislocation of the patella laterally exposing the articular surface of the patella.

Typically, guides or devices are used to assist the surgeon in removing the patella's articular surface. These devices include a plate adapted to engage an anterior surface of the patella opposite the articular surface. A template may then be positioned adjacent to the articular surface so that a cutting instrument, typically an oscillating saw may be guided over the articular surface forming a flat surface adapted to receive a patellar implant.

Patellar implants come in a variety of shapes and sizes, which are controlled by the manufacturer of the implant. The surgeon uses the patellar implants which are furnished with the particular total knee system that he/she has selected. The surgeon chooses the best size, and in some cases, has a choice of whether or not to use a metal-backed component. Every manufacturer supplies instrument and/or instructions for using generic instrumentation for preparing the patella surface to receive an implant. In preparing the surface on which the implant will rest or to which it will be cemented, a planar surface is usually desired. This is, with a few systems, a recessed planar surface in which case the implant is rounded rather than elliptical or irregular. This is the only type of system where the shape/size of the implant should correspond to the tooling used to produce the surface on which the implant rests.

The prior art guides severely limit the surgeon's freedom in deciding the shape of the patellar implant, since in many cases, the patellar implant manufacturer manufactures the corresponding guide for use in surgery. Unfortunately, the prior art guides can result in improperly and imprecisely oriented and shaped patellar surfaces adapted to receive the implant. This can result in an improper attachment of the implant to the remaining patella resulting in poor mechanics, and sometimes necessitating subsequent corrective surgery.

Some of the problems with prior art instrumentation are as follows:

1) There is no way of precisely determining orientation of the surface on which the patellar implant will rest;
2) In many cases, there is no provision for adjusting the orientation of the patellar implant;
3) There is an inability to cut a precisely planar surface; and
4) There is an inability to produce a recessed surface which has other than a circular border.

Therefore, an object of the present invention is to eliminate those problems.

A brief summary of the history of joint replacement technology is instructive in illustrating the problems addressed in this specification. The first reliably successful major total joint replacement procedures were not performed until the late 1950s when prosthetic components were first implanted in bone with the use of methylmethacrylate as a grouting agent. More recently, prostheses have been introduced without grouting agents, and naturally the "press-fit" of such prosthetic implants must be more exacting to give successful results. Unfortunately, because the gap between bone and implant should not be more than about 0.005 inches, typical bone preparation methods including broaching, reaming and sawing usually result in gaps of typically 0.050 inches between prosthesis and bone. This has led to a standard practice of impacting slightly oversized prosthetic implants into bone sites to improve fit, but this in turn often causes bone fractures and even this method cannot eliminate all gaps.

It would be desirable, in view of the above, to be able to produce customized bone preparation sites to receive specific prosthetic implants. For example, it would be advantageous to produce a planar surface at the patellar and tibial surfaces of the knee, which planar surface is recessed slightly into the bone, so as to correspond with the outer border of the implant. This is not possible with an oscillating saw; as discussed previously, some patellar implants are available which have a circular cross section (which represents a compromise) to allow the use of a cylindrical reamer to provide the implantation site. Other implants require similar specialized bone site preparation, although techniques to achieve this have heretofore been unavailable.

Thus, a need remains for a method and apparatus for machining bone, such as the patella, to fit an orthopedic surgical implant that gives substantial freedom for the surgeon in defining (1) where to place the implant; (2) the orientation of the implant; and (3) how to machine the bone to result in a good fit between the bone and the implanted prosthesis.

SUMMARY OF THE INVENTION

My invention is an apparatus for retaining a bone site in a fixed position and guiding a high speed power tool for machining the bone at this site. The apparatus includes a positioner frame for rigid attachment about the bone site and a power tool mount attached to the frame adapted to receive a power tool for machining the bone in a predetermined manner. The frame has a bone clamping mechanism capable of adjusting the placement and orientation of the bone site relative to the frame.

The clamping mechanism includes at least one gripper attached to the frame for clamping the bone. Preferably, the clamping mechanism includes a plurality of grippers spaced about the positioner frame for clamping the bone at multiple locations, such as three grippers, or four grippers equally spaced at 90° intervals. A pedestal connects to the positioner frame upon which the bone rests, wherein the clamping mechanism is capable of moving the bone relative to the pedestal. Movement of the bone is achieved by a plurality of slider assemblies.

Each slider assembly includes a support with a pair of parallel and spaced walls with aligned slots and slider clamps radially operable within the slots to clamp the bone. An upper member is provided for engaging the slot and sliding in the slots. A lower member having a clamping end is spaced from and is affixed to the upper member at a location remote from the clamping end. An adjustment screw threadably engages to the upper member. The adjustment screw includes a distal end for engaging the lower member at a location between the clamping end and the remote location.

A vertically oriented power tool mount is secured to the positioner frame through a post, so that a power tool can be pivotally mounted to the post. The power tool mount includes a power tool receiving member that is slidably received by the post so that the power tool receiving member can move relative to the post. A hinge plate attaches to the post. A hinge is pivotally connected to the hinge plate through a hinge pin. The hinge includes a sleeve to accommodate a power tool. An adjustable stop is threadably received by the post for limiting the vertical movement of the power tool receiving member. A power tool for machining bone is received by the power tool mount at the sleeve.

The power tool mount also includes a power tool receiving member slidably received by the post so that the power tool receiving member can move vertically relative to the post. An adjustable stop is secured to the post for limiting the vertical movement of the power tool receiving member. Preferably, the stop is threadably received by the post. An arrangement is provided for measuring a vertical distance between an end of a machining bit received by the power tool relative to the frame. This arrangement includes a plurality of marks positioned on the post and a sleeve received by the post and adapted to move vertically and coact with the marks. The marks correlate to a vertical distance between the frame and a machining bit received by the power tool.

A machining bit is received by the power tool. The bit is adapted for side cutting and end cutting. In one embodiment, this bit includes a shaft adapted to be rotated by the power tool about a longitudinal axis passing through the shaft and a cutter positioned at an end of the shaft. The cutter is formed by a plurality of radially extending cutting edges extending from a center of the cutter, through which the longitudinal axis passes and a plurality of longitudinally extending cutting edges. A depth adjuster includes a series of depressions, each of a desired depth formed along a side of a positioner frame. The depth adjuster also includes a depth adjustment gauge having a series of depth indications, each at a desired level on the positioner frame. The depth adjuster is adapted to cooperate with a power tool for controlling the depth of a cut.

A template corresponding to a predetermined manner (i.e., shape) attaches to the positioner frame for guiding the power tool. The template is attached to an upper surface of the positioner frame, so as to locate a cutout portion of the template in a centered relationship over the bone to be mounted on the pedestal. The template cutout can be elliptical in shape or any other shape.

Further, my invention includes a method for reconstructive knee surgery including the steps of making an incision of the skin of the knee positioned adjacent the patella; everting and dislocating the patella thereby exposing the articular surface of the patella; placing the anterior surface of the patella on a pedestal; gripping and orienting the articular surface of the patella using gripping assemblies, placing a template over the articular surface of the patella; machining a surface of the patella with a bit coacting with the template thereby forming a machined area; and securing a patellar implant to the machined area.

BRIEF DESCRIPTION OF THE DRAWINGS

FIG. 2b is an exploded view of the apparatus shown in FIG. 2a;

FIG. 3 is a top view of a base of the apparatus shown in FIG. 2a;

FIG. 4 shows a side view of a slider assembly of the apparatus shown in FIG. 2a;

FIG. 6 is a top view of a patella insert pattern of the apparatus shown in FIG. 2a;

FIG. 7a is an exploded view of a surgical rotary power source support arm of the apparatus shown in FIG. 2a;

FIG. 7b is a section taken along lines VIIb—VIIb in FIG. 7a;

FIG. 7c is a section taken along lines VIIc—VIIc in FIG. 7a;

FIG. 8a shows a side view of a machining bit for use with a rotary power source for use in the apparatus shown in FIG. 2a;

FIG. 8b shows a bottom view of the bit shown in FIG. 8a;

FIG. 8c shows a top view of the bit shown in FIG. 8a;

FIG. 10 is a side view of a knee during patella replacement surgery wherein a recessed surface is shown on the patella made by the apparatus shown in FIG. 2a.

DESCRIPTION OF THE PREFERRED EMBODIMENTS

Figure 1:
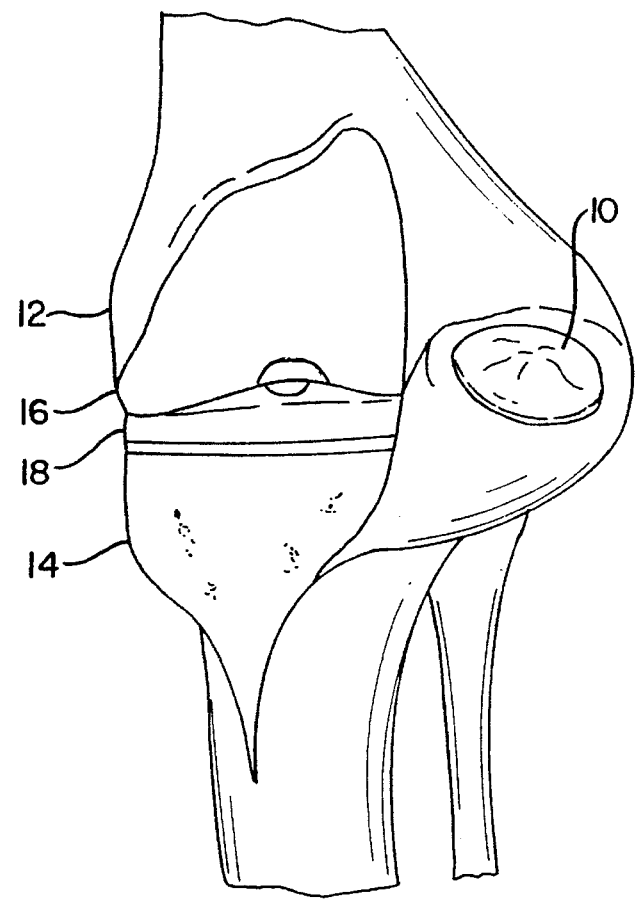
FIG. 1 is a side view showing a knee having a prosthetic device planted therein and an exposed patella.

FIG. 1 shows an exposed patella 10 during a knee replacement surgery. The knee is approached through a longitudinal skin incision, followed by a medial parapatellar capsular incision. The quadriceps tendon is incised longitudinally, allowing eversion and dislocation of the patella 10 laterally exposing the tibia 14 and the femur 12. Typically, prosthesis implants 16 and 18 are attached to the femur 12 and tibia 14 before the patella 10 is surgically machined for an implant.

Figure 2A:
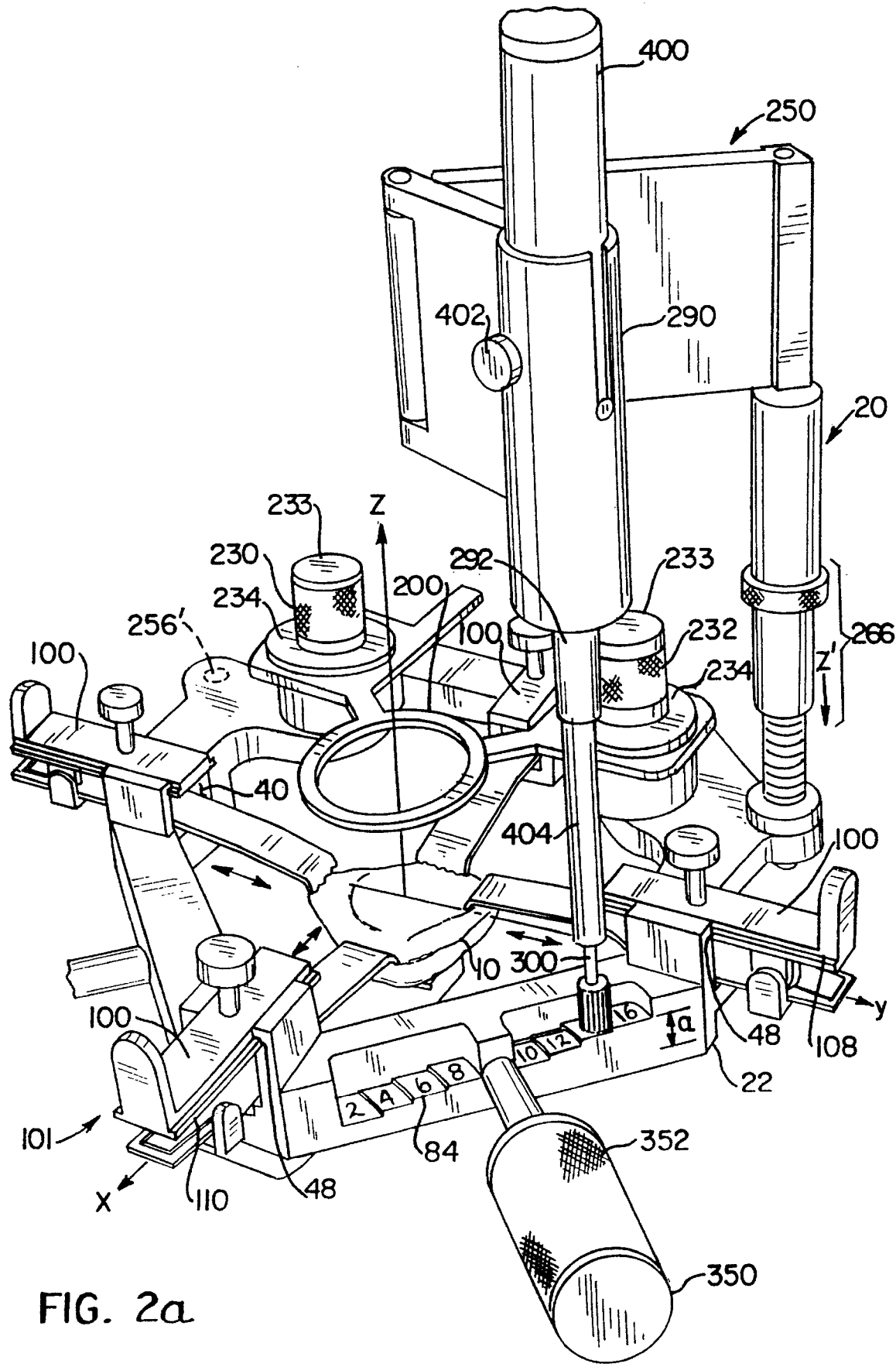
FIG. 2a is a top perspective view of an apparatus for machining bone to fit an orthopedic surgical implant made in accordance with the present invention.
Figure 2B:
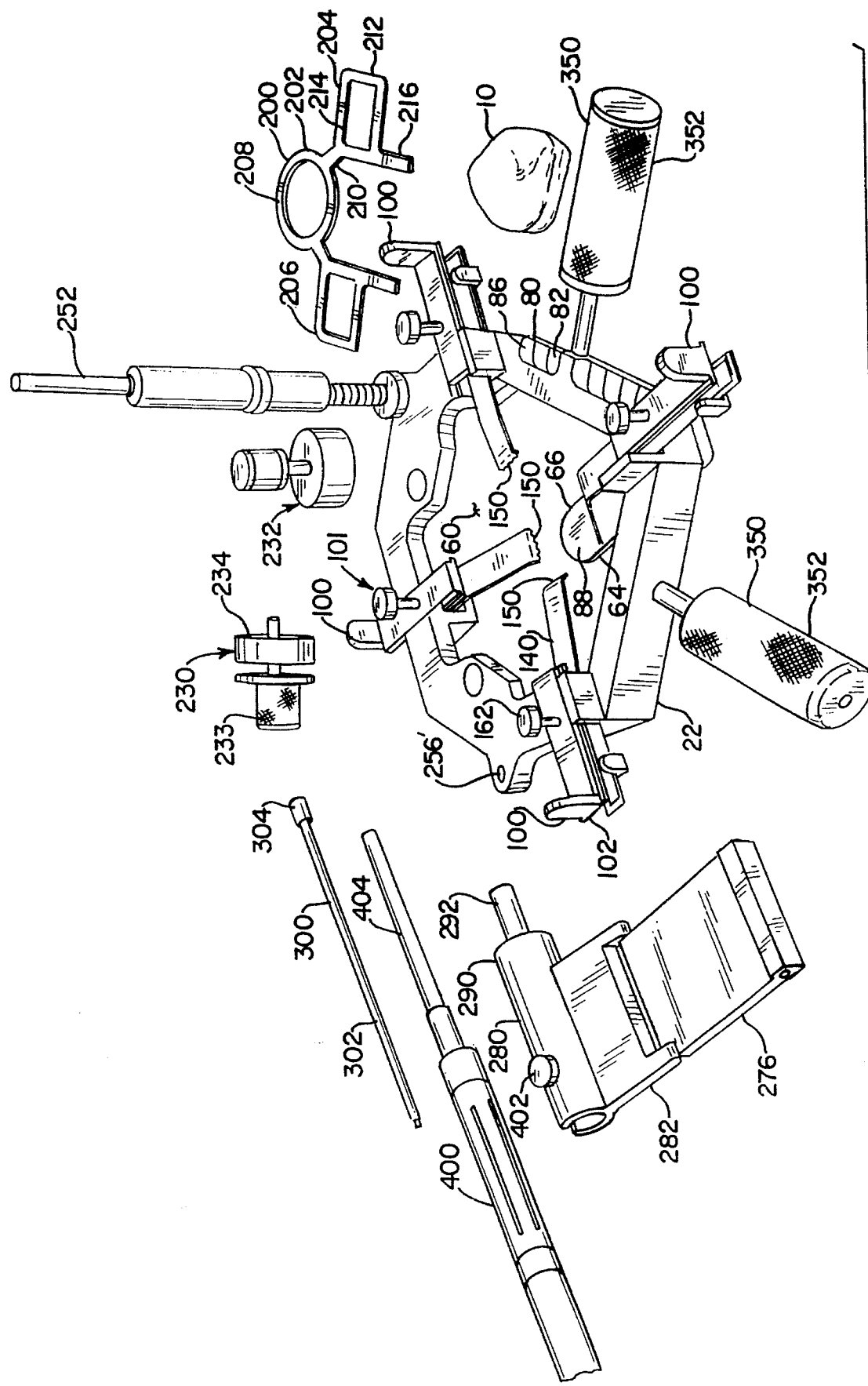
Figure 3:
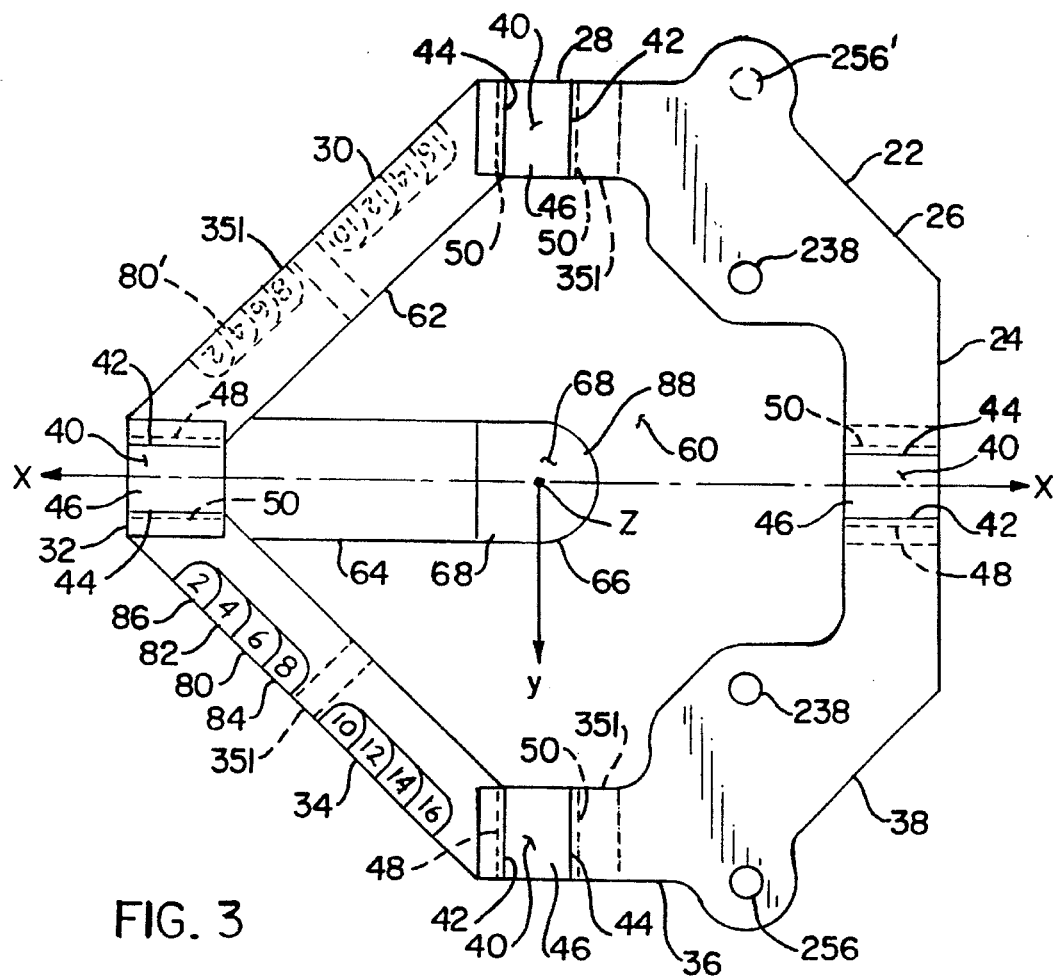

FIGS. 2a and 2b show an apparatus for retaining a bone site in a fixed position and guiding a high-speed power tool for machining bone to fit a surgical implant. As shown in FIGS. 2a, 2b and 3, the apparatus 20 includes a base or positioner frame 22 having eight integrally connected segments 24, 26, 28, 30, 32, 34, 36 and 38. Segments 24, 28, 32 and 36 are spaced apart from each other by approximately 90° intervals and each include a U-shaped slide clamp assembly slot 40. Each slot 40 includes a first wall 42 and a parallel spaced apart second wall 44, which depend from a base wall 46. Wall 42 defines a U-shaped slot 48 and wall 44 defines a U-shaped slot 50. Slots 48 and 50 are spaced directly apart from and aligned with each other.

A patella receiving opening 60 is defined by an inner wall 62 formed by segments 24, 26, 28, 30, 32, 34, 36 and 38. A patella receiving arm 64 attaches to segment 32 below its associated slot 40 and extends radially toward the center of opening 60. A rectangularly shaped pedestal 66 having a rounded end attaches to an end of the patella receiving arm 64 and is located approximately in a central position 68 of the patella receiving opening 60. The pedestal 66 is adapted to permit the patella 10 to rest thereon. An "X" axis passes through the center of the opening 60 and through the respective slots 40 of segments 24 and 32. A "Y" axis also passes through the center of the opening 60 at right angles to the X axis and in the same plane. A "Z" axis is normal to the X-Y plane and also passes through the center of opening 60. The base 22 is symmetrical about a plane containing the X axis and the Z axis, with the exception of a depth adjustment gauge 80 formed along a side of segment 34. Preferably, a depth adjustment gauge 80', which is shown in phantom in FIG. 3 and is the same as depth adjustment gauge 80, should also be formed and segment 30 so that the base 22 is symmetrical about the plane containing the X axis and Z axis.

Depth adjustment gauge 80 includes a plurality of steps or depressions 82. Upper surfaces 86 of the steps 82 are spaced apart in the Z axis direction corresponding to a desired depth. As shown in FIG. 2a, a series of indicia or depth indications 84 are provided with the steps to correlate a desired level on the positioner frame 20 or a distance "a" in the Z axis direction between the upper surface 86 of a respective step and an upper surface 88 of the pedestal 66.

As shown in FIGS. 2a and 2b, four slider clamp assemblies or grippers 100 are provided, which form a clamping mechanism 101 for clamping, adjusting and orienting the patella 10 relative to the base 22 and the pedestal 66. The clamp assemblies 100 are spaced about the base 22 and clamp the patella at multiple locations. Each slider clamp assembly 100 passes through a respective slot 40 and is adapted to hold the patella 10 against the upper surface 88 of the pedestal 66. Although the four slider clamp assemblies are equally spaced at 90° intervals as shown, other arrangements could be used, such as two or three slider clamp assemblies. The clamp assemblies 100 are adapted to be spaced about a bone site and permitting incremental adjustment of the bone site's orientation about two orthogonal axes and moving the bone site in two orthogonal directions relative to the pedestal 66.

Figure 4:
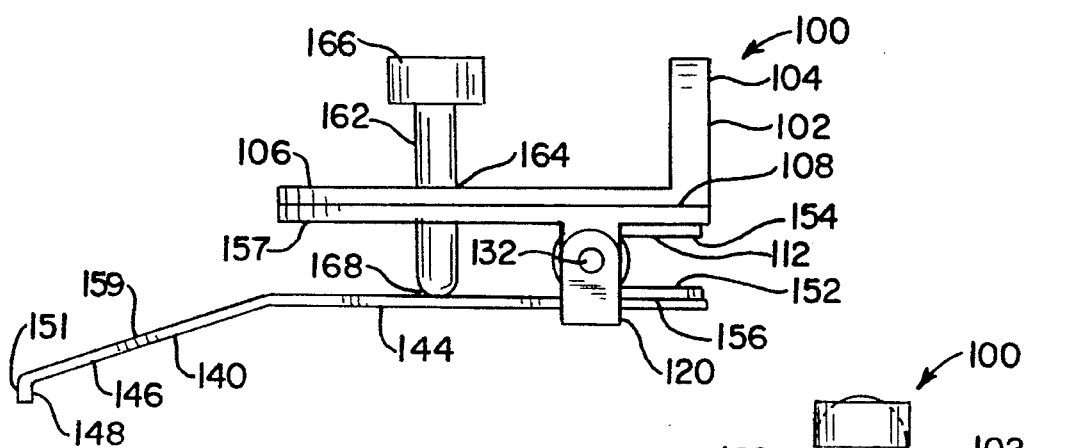
Figure 5:
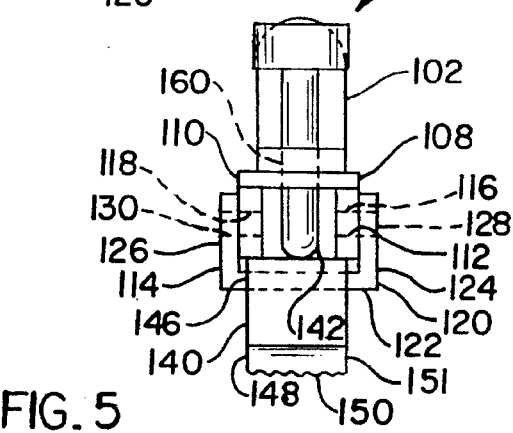
FIG. 5 is a front view of the slider assembly shown in FIG. 4.

As shown in FIGS. 4 and 5, each clamp 100 includes an L-shaped arm or upper member 102 having a first segment 104 and a second segment 106 normal thereto. Rails 108 and 110 extend from opposite sides of segment 106. Rails 108 and 110 are adapted to be slidably received in walls 42 and 44 of respective slots 48 and 50. Walls 42 and 44 support segment 106 so that each slider clamp assembly 100 is radially operable within the slots. Integral legs 112 and 114 extend from segment 106. Coaxial holes 116 and 118 are defined by legs 112 and 114, respectively. A U-shaped bracket 120 attaches to arm 102 and includes a base 122 and two extending legs 124 and 126. Coaxial holes 128 and 130 are defined in legs 124 and 126. A shaft 132 passes through holes 116, 118, 128 and 130. More specifically, shaft 132 is press fit onto legs 124 and 126 and shaft 132 is slidably received by legs 112 and 114.

A segmented hold down arm or lower member 140 passes through a slot 142 defined by base 122 and legs 124 and 126 of bracket 120. Arm 140 includes a first segment 144, which passes through slot 142, a second segment 146 integrally attached at one end of segment 144 and a third segment 148 integrally attached at an end of segment 146. A plurality of teeth 150 are defined at a clamping end 151 in segment 146, which are adapted to engage an upper surface of the patella 10. Hence, the arm 140 is spaced from and affixed to arm 102 by the bracket 120 at a location remote to the clamping end 151.

A torsional spring 152 having a coiled portion and two legs 154 and 156 is received by the shaft 132. Leg 154 abuts against a surface 157 of arm segment 106 and leg 156 abuts against a surface of hold down arm segment 144. This arrangement applies a rotating moment against hold down arm 140.

Segment 106 also defines a threaded hole 160, which passes therethrough. A threaded adjustment screw 162 is provided and includes a threaded shaft 164 having a knurled head 166 at one end and a tip 168 at a distal end. The threaded shaft 164 passes through hole 160 and is threadably engaged to segment 106. Tip 168 is adapted to engage with upper surface 159 of segment 144 at a location between the clamping end and the bracket 120.

Figure 6:
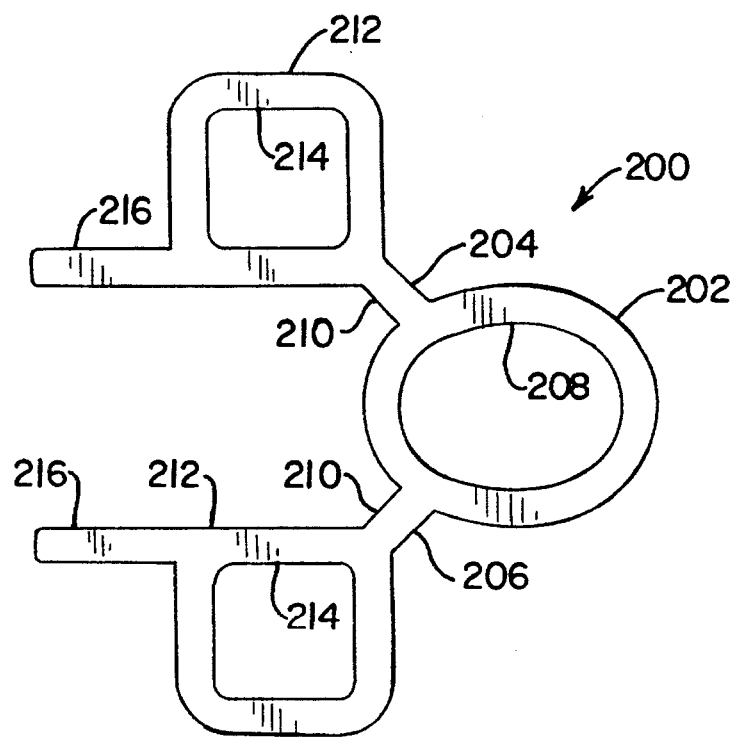

As shown in FIGS. 2a, 2b and 6, the apparatus 20 also includes a patella insert pattern or template 200 having a sculpting ring 202 with two integral legs 204 and 206 extending therefrom. The sculpting ring 202 includes an inner guide surface 208 that defines a cutout area that can take many shapes, such as elliptical as shown, circular, curvilinear or any other shape which corresponds to an outside profile of a patellar insert and correspond to a predetermined cut for guiding a power tool. Legs 204 and 206 each include a leg segment 210 extending from ring 202. An adjustment ring 212 extends from segment 210 and includes an inner surface 214 that defines a square profile or any other shaped profile. An adjustment handle 216 extends from the adjustment ring 212.

As shown in FIG. 2a, the patellar insert pattern 200 is secured to the base 22 by two plate arrangements 230 and 232. Each plate arrangement includes a bolt 233, having a head and threaded shaft, and a plate 234 having a central hole passing therethrough. The bolt shaft passes through the plate hole and the hole defined by the adjustment ring inner surface 214 and is threadably received by the base 22 within a threaded hole 238, see FIG. 3 also. The adjustment ring 212 and plate 232 are sandwiched between the head of bolt 233 and an upper surface of the base 22. The hole area defined by each adjustment ring is larger than the diameter of the shaft of bolt 233. Hence, the position of the sculpting ring 202 can be moved about in the X and Y direction over the patella before the bolts 233 are tightened and the pattern 200 held in place. This enables the patella insert pattern 200 to be properly aligned over the patella.

As shown in FIGS. 2a, 2b, 7a, 7b and 7c, the apparatus 20 also includes a rotary power source support arm (or power tool mount) 250, which is secured to base 20. The rotary power source support arm 250 includes a support post 252 extending along a vertical axis in the Z direction having an elongated cylindrical shaft terminating in a threaded end 254. The threaded end 254 is threadably engaged to base 22 through one of two holes 256 and 256'. Preferably, the threaded end 254 is received by hole 256 if gauge 80 is used and threaded end 254 is received by hole 256' (in phantom) if gauge 80' is used. The support post 252 also includes a first cylindrical hinge receiving section 258, a partially threaded middle section 260 that has a greater diameter than section 258, and a lower section 262 that includes a stop 264 and the threaded end 254. Annular calibration marks 265 are positioned on the support post 252 between the threaded middle section 260 and the stop 264. The marks 265 are spaced 1 m.m. apart with every fifth mark being wider than those positioned therebetween.

A partially threaded collar 266 is threadably received by the threaded middle section 260. The collar 266 is threaded internally at an upper portion so as to engage the threaded portion of section 260. A lower portion of the collar 266 is bored so that a portion of the support post having the calibrated marks 265 passes therethrough. The collar 266 includes an upper knurled ring 267. A partially threaded cylindrically shaped sleeve 268 is threadably received by the threaded portion of the middle section 260. The sleeve 268 includes a knurled outer surface. The sleeve 268 is threaded internally at a lower portion to engage the threaded portion of section 260. An upper portion of the sleeve 268 is bored so that a portion of section 258 passes therethrough. The collar 266, sleeve 268 and calibration marks 265 form a hinge piece height adjustment arrangement.

A hinge piece 270 having hollow sections 272 and 274 at opposite ends and a central integral plate 276 is slidably received by the hinge section 258 of the support post 252. Specifically, the cylindrical hinge section 258 slidably passes through the hollow section 272 of hinge piece 270 so that it is pivotally attached to section 258.

The support arm 250 also includes a hinge sleeve 278 having a motor sleeve 280 which is adapted to receive a rotary power source. Sleeve 280 integrally attaches to a plate portion 282, which in turn is integrally attached to two spaced apart cylindrical sleeves 284, 286. Hollow cylindrical section 274 is received between cylindrical sleeves 284, 286 so that the hollow sections are coaxially aligned. A hinge pin 288 passes through the sleeves 284 and 286, bearings 289 and section 274, thereby pivotally securing hinge sleeve 278 to hinge piece 270 so that both hinge sleeve 278 and hinge piece 270 can pivot about pin 288. Also, sleeve 280 is slidably received by the post 252 so that the sleeve 280 can move vertically relative to the post.

Figures 8A, 8B, 8C:
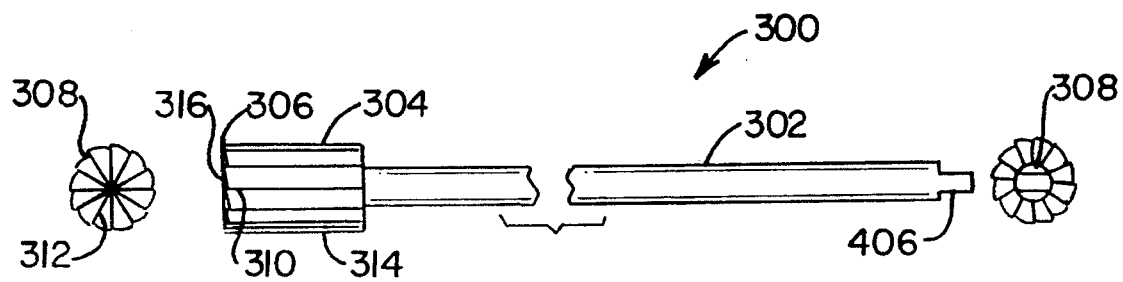

As shown in FIGS. 2a and 2b, the sleeve 280 is adapted to receive a rotary power source such as the "65K Universal Instrument" manufactured by The Anspach Effort, Inc., of Lake Park, Fla. The rotary power source includes a body adapted to be received and supported by an upper portion 290 of the sleeve 280 so that rotary power source is pivotally mounted to post 252. The rotary power source body is adapted to receive a machining bit 300, as shown in FIGS. 8a, 8b and 8c, which is adapted to pass through a lower portion 292 of the sleeve 280. Preferably, the machining bit is disposable and is used for only one surgical procedure. This minimizes cross contamination between patients by using the same bit 300.

Preferably, the machining bit 300 has an elongated shaft 302, and a cutter 304 at one end so that the machining bit 300 is adapted to rotate about an axis passing through the shaft 302 and the cutter 304. The cutter 304 has a plurality of longitudinally extending cutting blades or edges 306 (for side cutting about surface 314) and a plurality of radially extending bottom cutting blades or edges 308 (for end cutting about surface 316) with respective cutting surfaces or tips 310 and 312. The machining bit cutter 304 can be of any shape so long as it can simultaneously do side cutting and end cutting.

As shown in FIGS. 2a and 2b, multiple handles 350 are threadably secured to the base segments 30 and 34. Alternatively, handles 350 can be secured to base segments 28 and 36. Threaded holes 351 (see FIG. 3) are defined in side surfaces of segments 28, 30, 34 and 36, to threadably receive two or four guide handles 350, respectively. Each handle 350 includes a knurled portion 352 adapted to be held by an assistant to the surgeon so that the apparatus base 22 can be held in place during surgery on the patella. Typically, only one assistant would be needed to hold two of the handles 350. As stated previously, preferably the base 22 is symmetric about an X-Z plane. Thus, handles 350 can be positioned so that an assistant can hold two handles on either side of the X-Z plane so that the apparatus 20 can be easily used on both "left" and "right" knees.

As stated herein previously, the patella may be modified during knee replacement surgery. The knee is surgically approached adjacent to the patella through a medial parapatellar incision. The quadriceps tendon is then incised longitudinally, allowing eversion and dislocation of the patella laterally exposing the articular surface of the patella. After the femur and tibia are modified for a prothesis, then the surgeon decides whether a patellar implant is required.

If a patellar implant is required, then an anterior surface of the patella is placed on the upper surface 88 of the pedestal 66, as shown in FIG. 2a. More specifically, the pedestal can be slid between the respective tissue and anterior surface of the patella 10. The assistant then holds the apparatus 20 in place via handles 350. Then, the four slider clamp assemblies 100 are arranged to properly clamp the patella 10. The clamp arms 102 are radially moved toward and/or away from the center position of the patella receiving opening 88 defined by the base, so as to engage the teeth 150 of each segment 148 with the articular surface of the patella or adjacent tissue. Screws 162 are then tightened and/or loosened thereby adjusting the placement and orienting the articular surface of the patella 10 with respect to the pedestal 66, to the satisfaction of the surgeon and to hold the patella in place.

At this time, the surgeon then decides which patella insert pattern 200 to use. This depends, as stated earlier, which particular patellar implant would best serve the patient. In many cases, the surgeon cannot determine which particular implant that would best serve the patient until after the patella is exposed during surgery. The pattern 200 is loosely attached to the base via plates 234 and bolts 233. The pattern 200 is then positioned over the patella to correspond to the location where the surgeon will place the patellar implant. Bolts 233 are then tightened and the pattern 200 is held in place in a centered relationship over the pattern.

A surgical rotary power source 400, such as that previously discussed, is then received by sleeve 280 and is held in place by tightening of a screw 402, threadably received by sleeve 280, against the body of the rotary power source 400. A hollow sleeve 404 of the surgical rotary power source 400 is received by the lower portion 292 of the sleeve 280. The shaft 302 of bit 300 is slidably received by sleeve 404. An end 406 of bit 300 is then coupled to the rotary power source 400 in a manner well known in the art. Preferably, the outer diameter of the sleeve 404 and the cutter 304 are the same. The machining bit 300 extends along an axis in the Z direction which is parallel to the support post vertical axis. As can be seen in FIGS. 8a, 8b and 8c, the orientation of the particular bit is such that a level flat cut can be obtained via blades 308 as well as clean side cuts can be obtained via blades 306 when machining a recess in the patella to receive the patellar implant.

Figure 9:
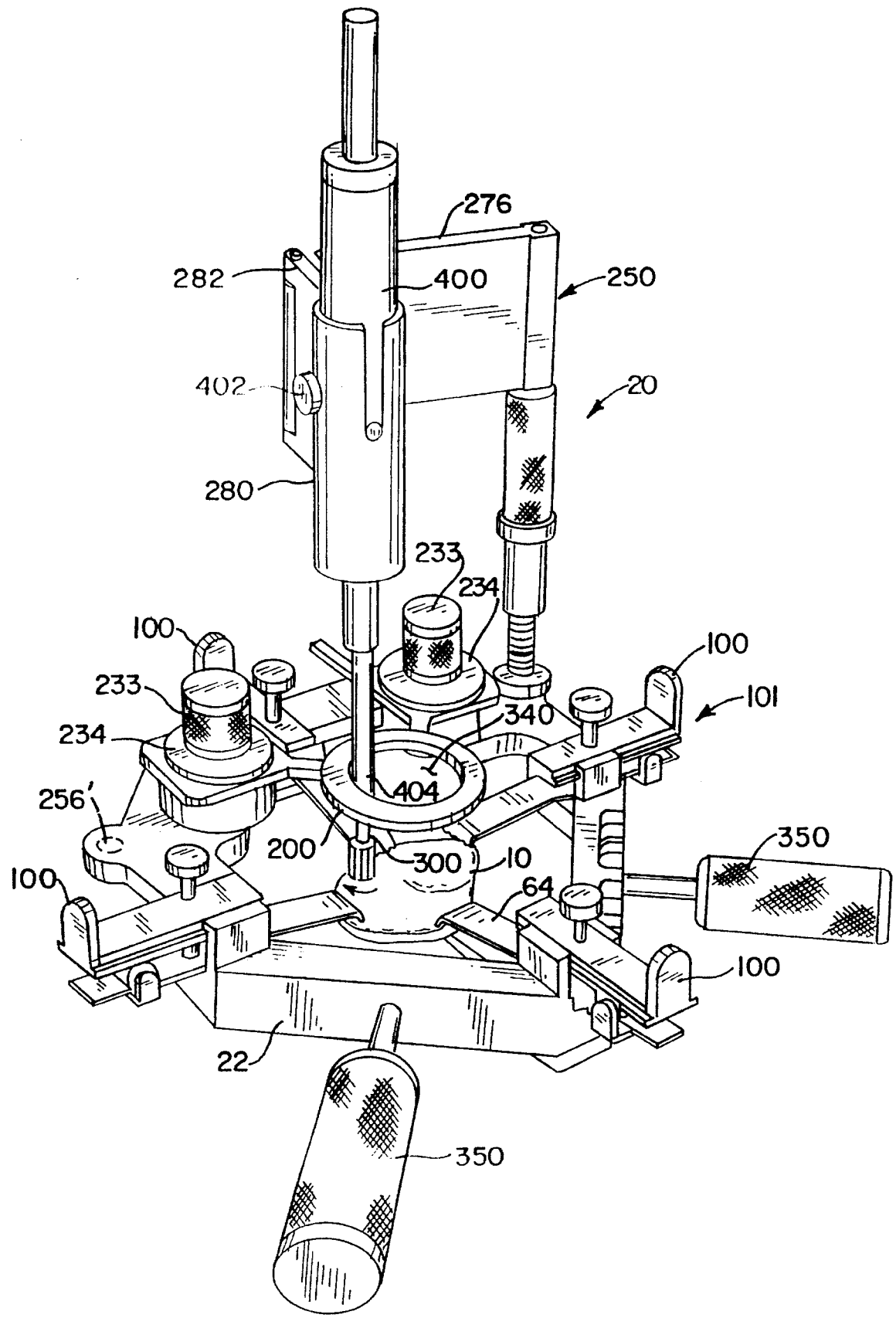
FIG. 9 shows a top prospective view of the apparatus shown in FIG. 2a wherein the patella is being reamed.

As shown in FIG. 9, the surgeon then moves the surgical rotary power source 400 via the apparatus arm 250 over the patella 10 and pedestal 66 so that the machining bit 300 comes in contact with an upper surface point or apex of the articular surface of the patella 10. However, in many cases, the articular surface of the patella has degraded and the surgeon places the bit 300 at a position above the patella corresponding to where the surgeon wants the apex of the implant articular surface to be located. The surgeon then, while holding the bit 300 in place, rotates the sleeve 268 so as to move it upward until the bearing 269 is sandwiched between the sleeve 268 and section 272. The sleeve 268 prevents the machining bit 300 from moving downwardly in the Z direction toward the pedestal 66, but still permits the machining bit 300 to be moved in an upwardly direction.

The surgeon then moves the rotary power source 400 and in turn the machining bit 300, hinge piece 270 and hinge sleeve 278 so that the machining bit 300 is positioned over to the depth gauge 80, as shown in FIG. 2a. The surgeon then rotates the collar 266 so as to move it upward until an upper surface of the knurled ring 267 abuts a lower surface of sleeve 268. At that time, the surgeon then determines the thickness of the patellar implant. This will correspond to an amount of the patella to be removed or reamed so that the implant is properly received by the patella.

The collar 266 is then rotated in the clockwise direction and moved downwardly in the Z-direction corresponding to the thickness of the patellar implant. Specifically, the surgeon counts off the number of calibration marks in a downwardly direction, that correspond in millimeters (m.m.) to the thickness of the patellar implant. For example, if the patellar implant is sixteen (16) m.m. thick, then the collar 266 would be rotated in the clockwise direction so that it travels to a level which is sixteen (16) one m.m. graduations lower in a similar manner as one would adjust the spindle on a micrometer caliper. Then the sleeve 268 is rotated in the clockwise direction until it abuts against the ring 267 of collar 266. The surgeon can then determine the thickness of the patella 10 that will remain after machining by observing which step 82 is at the level of the bit tip 310 when the hinge piece 270 rests on the bearing 269 (which in turn rests on the sleeve 268, which abuts the collar 266). The indicia 84 marked on the steps 82 correspond to the thickness in m.m. of the patella that will remain after machining or in other words, the distance of the machining tip 310 from the upper surface 88 of the pedestal 66. Thus, the sleeve 268, which is adapted to move in the vertical "Z" direction, coacts with the marks 265 that correlate to a vertical distance between the frame 22 and an end of the machining bit 300 received by the rotary power source 400.

If the surgeon realizes that the particular patellar implant would require too much of the patella to be removed, then the surgeon could choose a different insert using the same pattern 200 or a different pattern 200, which would correspond to an insert that would require less of the patella to be removed. Then the above process must be repeated. Hence, the depth adjustment gauge 80 and the hinge piece height adjustment arrangement (collar 266, sleeve 268, and the calibration marks 265) individually and in combination act as a depth adjuster and cooperate with the machining bit 300 and the rotary power source 400 to assist the surgeon in determining the depth of the patella cut. Further, the height adjustment arrangement assists the surgeon in measuring a vertical distance (in the "Z" direction) between an end of the machining bit 300 received by the rotary power source 400 relative to the positioner frame 22.

Next, the surgeon places the machining bit tip 310 against the patella 10 by moving the rotary power source 400 via the surgical support arm 250, as shown in FIG. 9. The rotary power source sleeve 404 is then positioned to come in contact with the inner guide surface 208 of the pattern 200. It is important that the cutting bit 304 does not come in contact with the pattern 200 during surgery because the rotating machining bit 300 would damage the pattern 200 and the machining bit 300. Further, it is preferable that the radius of the sleeve 404 is less than the radius of curvature of any point of the sculpting ring guide surface 208.

Figure 10:
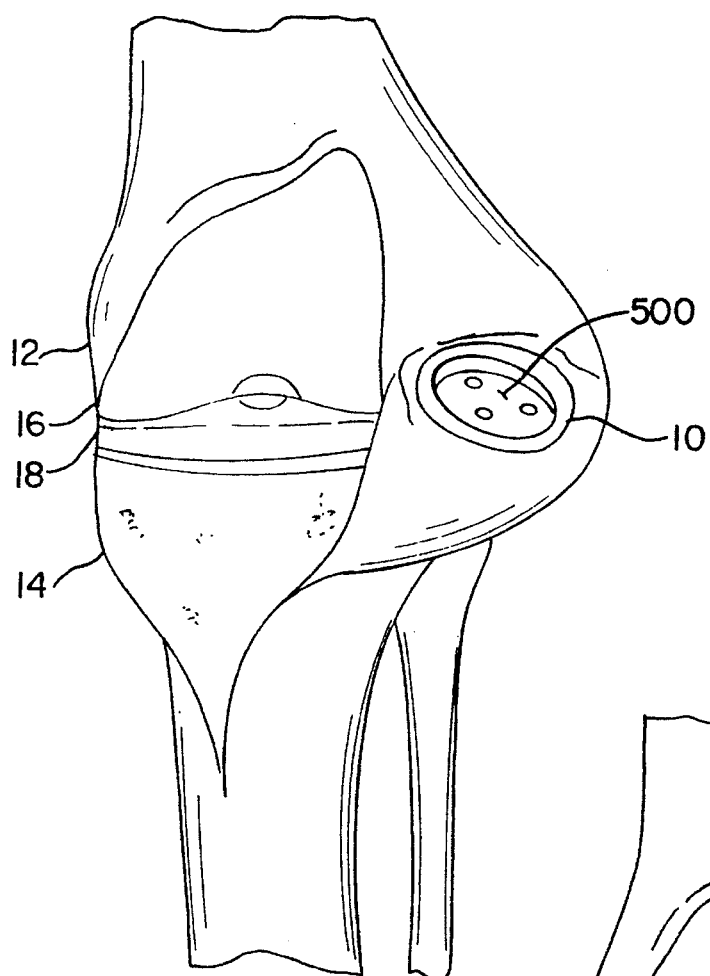

The surgical rotary power source 400 is then activated rotating the machining bit 300 about a longitudinal axis (parallel to the Z axis) passing therethrough. The sleeve 404 is then guided through the area within the inner perimeter of the sculpting ring guide surface 208 removing a portion of the patella. The rotary power source is lowered in the Z direction until the hinge piece bottoms out onto the height adjustment sleeve 268, which acts as an adjustable stop secured to the post 252 for limiting the vertical movement of the sleeve 280, and in turn the rotary power source 400 and machining bit 300. The machining bit 300 is then moved over the entire area of the pattern hole 340 defined by the sculpting ring 202 removing additional patella not removed when the machining bit was moved about the sculpting ring guide surface 208. Hence, a reamed hole or machined area 500, as shown in FIG. 10, is formed having an outer perimeter corresponding with the outer perimeter of the guide surface 208. At that point, the surgical rotary power source 400 is deactivated and the rotary power source 400 and the hinge piece 270 are raised so that the machining bit 300 is moved outside of the perimeter of the pattern 200.

At that time, the reamed surface of the patella is cleaned and inspected by the surgeon. As can be seen in FIG. 10, the machining bit 300 forms a recess having a flat base and perpendicular straight side walls. Next, the machining bit 300 is removed from the rotary power source and a pointed drill bit (not shown) is inserted. A second template is then placed over the pattern 200 identifying typically three holes that are to be drilled in the patella which are adapted to receive three locating pins of the patellar insert. The collar 266 and the sleeve 268 are adjusted in the downwardly direction Z' to determine the depth at which the holes are to be drilled. The rotary power source 400 is then activated and the drill bit passes through the respective holes of the second template and the respective locating pinholes are drilled in the patella. Next, the rotary power source 400 is deactivated, the second template is removed, the slider clamp assemblies 100 are loosened and the apparatus 20 is removed from the patella 10.

Alternatively, a second template having three locating pin holes could be provided. The second template has a perimeter corresponding to a perimeter of the patellar insert. A handle would be provided with the template so that the template could be placed within the recess 500. A hand-held drill having a drill bit and depth limiting collar, which is presently well known in the art, then can be activated by the surgeon so that the three locating pin holes can be drilled by the surgeon in the patella. Next, the drill is deactivated and the template is removed.

Then the appropriate implant can then be placed within the recess 500 in a manner well known in the art and the knee is then sutured.

The above-described apparatus 20 and method can be used for either a cemented patellar implant or a press fit patellar implant. Furthermore, using the above apparatus and described method, appropriate recesses and guide pinholes can be placed with an accuracy of ±0.005" of an inch, which is not capable in prior art devices. It is believed that this accuracy is on an order of magnitude better than that achievable by the prior art. This ensures a high integrity of the implant and minimizes the possibility of subsequent surgical techniques required to either replace the implant or to modify the patella due to improper fit. Further, apparatus 20 gives the surgeon substantial freedom as to where to place the implant, the orientation of the implant, how to machine the patella, and the shape of the implant. Furthermore, it is believed that the apparatus 20 need not be limited only to machining the patella, but could be used on other bones.

Having described the presently preferred embodiments of the present invention, it is to be understood that it may be otherwise embodied within the scope of the appended claims.

I claim:

1. An apparatus for retaining a bone site in a fixed position for machining the bone comprising:
   a) a positioner frame for rigid attachment about the bone site, said positioner frame having a bone clamping mechanism;
   b) a pedestal connected to said positioner frame, said pedestal having a contact surface adapted to have the bone site rest thereon, said bone clamping mechanism including a plurality of movable clamps spaced apart from said pedestal and adapted to contact the bone site and secure the bone site to the pedestal, wherein each said clamp is movable in a direction perpendicular to an axis perpendicular to the contact surface and incrementally adjustable in a direction parallel to said axis, and said clamps are adapted to be spaced about the bone site and permit incremental adjustment of the bone site's orientation about two orthogonal axes and moving the bone site in two orthogonal directions relative to said pedestal; and
   c) a power tool mount attached to said positioner frame adapted to receive a power tool for machining the bone.

2. The apparatus of claim 1 including a template corresponding to a predetermined manner of machining and attached to the positioner frame for guiding the power tool.

3. The apparatus of claim 2 wherein said template is attached to an upper surface of said positioner frame so as to locate a cutout portion of said template in a centered relationship over the bone to be mounted on said pedestal.

4. The apparatus of claim 3 wherein said template cutout is elliptical shaped.

5. The apparatus of claim 1 wherein each of said clamps including a gripping end for clamping the bone at multiple locations.

6. The apparatus of claim 1 wherein each of said movable clamps comprising a support having a pair of parallel and spaced walls with aligned slots and an arm movable within said slots to clamp the bone site.

7. The apparatus of claim 6 wherein each of said clamps further comprising an upper member for engaging and sliding in respective ones of said slots, a lower member having a clamping end and spaced from and affixed to said upper member at a location remote from said clamping end, and an adjustment screw threadably engaged to said upper member and having a distal end for engaging said lower member at a location between said clamping end and said remote location.

8. The apparatus of claim 1 wherein said power tool mount includes a post attached to said positioner frame and oriented vertically to said positioner frame so that a power tool can be pivotally mounted to said post.

9. The apparatus of claim 8 including a hinge plate attached to the post and a hinge pivotally connected through a hinge pin to said hinge plate, said hinge including a sleeve to accommodate a power tool.

10. The apparatus of claim 9 further comprising a power tool and a machining bit received by said power tool, said machining bit having a shaft adapted to be rotated about a longitudinal axis passing through said shaft and a cutter positioned at an end of said shaft, said cutter having a side cutting surface and an end cutting surface.

11. The apparatus of claim 10 wherein said cutter has a cutting surface formed by a plurality of radially extending cutting edges extending from a center of said cutter through which the longitudinal axis passes thereby forming said end cutting surface and a plurality of longitudinally extending cutting edges thereby forming said side cutting surface.

12. The apparatus of claim 8, wherein said power tool mount further comprises a power tool receiving member slidably received by said post so that said power tool receiving member can move vertically relative to said post, and an adjustable stop secured to said post for limiting the vertical movement of said power tool receiving member.

13. The apparatus of claim 12 wherein said adjustable stop is threadably received by said post.

14. The apparatus of claim 8 further comprising a plurality of marks positioned on said post and a sleeve received by said post and adapted to move vertically and coact with said marks, which correlate to a vertical distance between said positioner frame and an end of a machining bit received by the power tool.

15. The apparatus of claim 1 further including depth adjuster means for cooperating with a power tool for controlling the depth of cut.

16. The apparatus of claim 15, wherein said depth adjuster means comprises a depth adjustment gauge having a series of depressions, each of a desired depth formed along a side of the positioner frame, wherein said depth adjustment gauge is adapted to cooperate with the power tool.

17. The apparatus of claim 15 wherein said depth adjuster means comprises:

a depth adjustment gauge having a series of depth indications, each at a desired level on the positioner frame, wherein said depth adjustment gauge is adapted to cooperate with the power tool.

18. The apparatus of claim 1 further comprising a power tool for machining bone received by said power tool mount.

19. The apparatus of claim 1 including at least three clamps.

20. The apparatus of claim 1 including four clamps equally spaced at 90° intervals about said pedestal.

21. The apparatus of claim 1 further comprising:

means for measuring a vertical distance between an end of a machining bit received by a power tool relative to said positioner frame.

22. The apparatus of claim 1 further comprising a power tool received by the power tool mount and a disposable machining bit attached to said power tool.

23. An apparatus for retaining a bone site in a fixed position and guiding a high-speed power tool for machining the bone comprising:
   a) a positioner frame for rigid attachment about the bone site, said positioner frame having a bone clamping mechanism capable of adjustment and orientation of the bone site relative to said positioner frame;
   b) a power tool mount attached to said frame adapted to receive a power tool for machining the bone in a predetermined manner; and
   c) a template corresponding to the predetermined manner and attached to the positioner frame for guiding the power tool, wherein said template is attached to an upper surface of said positioner frame so as to locate a cutout portion of said template in a centered relationship over the bone to be mounted on the pedestal, wherein said template cutout is elliptical in shape.

24. An apparatus for retaining a bone site in a fixed position and guiding a high-speed power tool for machining the bone comprising:
   a) a positioner frame for rigid attachment about the bone site, said positioner frame having a bone clamping mechanism capable of adjustment and orientation of the bone site relative to said positioner frame, said bone clamping mechanism including a plurality of slider assemblies, each slider assembly comprising a support having a pair of parallel and spaced walls with aligned slots and slider clamps movable within said slots to clamp said bone, each of said slider clamps comprising an upper member for engaging and sliding in respective ones of said slots, a lower member having a clamping end and spaced from and affixed to the upper member at a location remote from the clamping end, and an adjustment screw threadably engaged to said upper member and having a distal end for engaging the lower member at a location between the clamping end and said remote location; and
   b) a power tool mount attached to said frame adapted to receive a power tool for machining the bone in a predetermined manner.

25. An apparatus for retaining a bone site in a fixed position for machining the bone comprising:
   a) a positioner frame for rigid attachment about the bone site, said positioner frame having a bone clamping mechanism;
   b) a pedestal connected to said positioner frame, said pedestal having a contact surface adapted to have the bone site rest thereon, said bone clamping mechanism including a plurality of movable clamps spaced apart from said pedestal and adapted to contact the bone site and secure the bone site to the pedestal, wherein each said clamp is movable in a direction perpendicular to an axis perpendicular to the contact surface and incrementally adjustable in a direction parallel to said axis, and said clamps are adapted to be spaced about the bone site and permit incremental adjustment of the bone site's orientation about two orthogonal axes and moving the bone site in two orthogonal directions relative to said pedestal; and
   c) a power tool mount attached to said frame adapted to receive a power tool for machining said bone, said power tool mount adapted to enable a power tool to be moved freely by a user in three dimensions relative to said pedestal.

26. An apparatus for retaining a bone site in a fixed position for machining the bone comprising:
   a) a positioner frame for rigid attachment about the bone site, said positioner frame having a bone clamping mechanism, said bone clamping mechanism including a plurality of movable clamps, each clamp comprising a support having a pair of parallel and spaced walls with aligned slots and slider clamps radially operable within said slots to clamp the bone;
   b) a pedestal connected to said positioner frame, said pedestal having a contact surface adapted to have the bone site rest thereon, said clamps spaced apart from said pedestal and adapted to contact the bone site and secure the bone site to the pedestal, wherein each said clamp is movable in a direction perpendicular to an axis perpendicular to the contact surface and incrementally adjustable in a direction parallel to said axis, and said movable clamps are adapted to be spaced about said bone site and permit incremental adjustment of the bone site's orientation about two orthogonal axes and moving the bone site in two orthogonal axes relative to said pedestal; and
   c) a power tool mount attached to said positioner frame adapted to receive a power tool for machining the bone.

27. An apparatus for retaining a bone site in a fixed position for machining the bone comprising:
   a) a positioner frame for rigid attachment about the bone site, said positioner frame having a bone clamping mechanism, said bone clamping mechanism including a movable clamp;
   b) a pedestal connected to said positioner frame, said pedestal adapted to have the bone site rest thereon, said clamp spaced apart from said pedestal and adapted to contact the bone site and secure the bone site to the pedestal, said movable clamp capable of moving and orienting the bone site on said pedestal relative to said positioner frame; and
   c) a power tool mount attached to said positioner frame adapted to receive a power tool for machining the bone, wherein said power tool mount includes a post attached to the positioner frame and oriented vertically to said positioner frame so that a power tool can be pivotally mounted to said post, a power tool receiving member slidably received by said post so that said power tool receiving member can move vertically relative to said post, and an adjustable stop secured to said post for limiting vertical movement of said power tool receiving member.

* * * * *